(12) United States Patent
Michelson

(10) Patent No.: US 8,922,373 B2
(45) Date of Patent: Dec. 30, 2014

(54) SELF ANCHORING IMPLANTABLE IDENTIFICATION MICROCHIP FOR USE IN ANIMALS

(75) Inventor: Gary Karlin Michelson, Los Angeles, CA (US)

(73) Assignee: Foundation Animals Foundation, Inc., Los Angeles, CA (US)

( * ) Notice: Subject to any disclaimer, the term of this patent is extended or adjusted under 35 U.S.C. 154(b) by 442 days.

(21) Appl. No.: 13/440,825

(22) Filed: Apr. 5, 2012

(65) Prior Publication Data
US 2013/0267962 A1 Oct. 10, 2013

(51) Int. Cl.
*G08B 13/14* (2006.01)
*A61B 19/00* (2006.01)

(52) U.S. Cl.
USPC .......... 340/572.1; 128/899; 600/486; 606/46; 606/117

(58) Field of Classification Search
CPC ... A01K 11/006; A01K 11/005; A61B 17/00; A61B 19/54; A61B 2019/5408; A61B 2019/5487; A61M 37/0076; A61M 16/0472; A61M 16/0465; A61M 2209/06; A61M 16/0497; A61M 2016/0429
USPC .............. 340/572.1, 10.1; 128/898, 899, 903; 600/325, 332, 485, 486, 488, 561, 564; 606/45, 46, 47, 116, 117, 155, 213
See application file for complete search history.

(56) References Cited

U.S. PATENT DOCUMENTS

| | | |
|---|---|---|
| 5,211,129 A | 5/1993 | Taylor et al. |
| 6,689,056 B1 | 2/2004 | Kilcoyne et al. |
| 6,746,404 B2 | 6/2004 | Schwartz |
| 7,411,492 B2 | 8/2008 | Greenberg |
| 7,965,188 B2 | 6/2011 | Geissler |
| 7,978,079 B2 | 7/2011 | Geissler et al. |
| 2002/0077555 A1* | 6/2002 | Schwartz ................ 600/486 |
| 2003/0050595 A1 | 3/2003 | Campbell |
| 2003/0229452 A1 | 12/2003 | Lewis et al. |
| 2006/0030847 A1* | 2/2006 | McGuckin et al. ............ 606/47 |
| 2006/0143302 A1 | 6/2006 | Welsh |
| 2006/0224625 A1 | 10/2006 | Warner |
| 2007/0226257 A1 | 9/2007 | Yarnall, Jr. |
| 2008/0244413 A1 | 10/2008 | Sampson et al. |
| 2009/0206996 A1 | 8/2009 | Masin et al. |
| 2011/0077659 A1 | 3/2011 | Mandecki et al. |

* cited by examiner

*Primary Examiner* — Omer S Khan
(74) *Attorney, Agent, or Firm* — Martin & Ferraro, LLP

(57) ABSTRACT

A device and method for subcutaneously implanting an identification chip into a domestic animal, the identification chip becoming relatively immobile once implanted.

42 Claims, 4 Drawing Sheets

SELF ANCHORING IMPLANTABLE IDENTIFICATION MICROCHIP FOR USE IN ANIMALS

FIELD OF THE INVENTION

The present invention generally relates to an implantable identification device for use in animals such as cats, dogs and livestock.

BACKGROUND OF THE INVENTION

Pets fulfill an important and emotional need in many households. Losing a pet can profoundly affect a family. Many lost pets end up at animal shelters and are eventually euthanized because the owner cannot be found. This has tragic consequences, not only for the pet being euthanized, but also for the pet's family, who suffers the loss of the pet.

In recent years it has become more popular to microchip a pet so that should the pet become lost, when found, it can be identified and returned to the owner. Such implantable microchips inserted through a trochar needle are commonly in use to identify livestock and pets such as cats and dogs. A problem has been that the chips do not always remain where they have been implanted, which can render the chip unreadable, negating any benefit and defeating the intent of making the animal identifiable. Accordingly, there exists a need for an implantable chip which may be safely anchored into the site of implantation.

SUMMARY

The present invention in one preferred embodiment provides for a self-anchoring, implantable identification device for use in identifying an animal. The device includes a capsule having a leading end with a forward facing surface, a trailing end, a mid-longitudinal axis through the leading and trailing ends, a length from the leading end to the trailing end along the mid-longitudinal axis, and a maximum width perpendicular to the mid-longitudinal axis. The device has a microchip sized and configured for placement in the capsule of the device, the microchip being configured to store identification information unique to the microchip for identification of the animal into which the device is implanted, the identification information including at least one of text, symbols, and numbers. The device further includes a transmitter for transmitting the identification information stored on the microchip; an antenna operatively connected to the transmitter; and at least one retention member extending from the forward facing surface of the leading end of the capsule, the retention member having a proximal portion and a distal portion with a free end. The retention member is biased to move from an undeployed position where the free end is located at a first distance from the mid-longitudinal axis of no more than one-half the maximum width of the capsule to a deployed position where the free end is located at a second distance from the mid-longitudinal axis of more than one-half the maximum width of the capsule so that the free end of the distal portion penetrably engages tissue after the device is implanted into the animal.

In a further preferred embodiment, the invention provides for a self-anchoring, implantable identification device for use in identifying an animal. The device includes a capsule having a leading end, a trailing end, a mid-longitudinal axis through the leading and trailing ends, a length from the leading end to the trailing end along the mid-longitudinal axis, and a maximum width perpendicular to the mid-longitudinal axis. The device has a microchip sized and configured for placement in the capsule of the device. The microchip is configured to store identification information unique to the microchip for identification of the animal into which the device is implanted, the identification information including at least one of text, symbols, and numbers. The device further includes a transmitter for transmitting the identification information stored on the microchip; an antenna operatively connected to the transmitter; and at least one retention member extending from the capsule of the device, the retention member having a proximal portion and a distal portion with a free end, the retention member having a maximum length that is less than the length of the capsule. The retention member is biased to move from an undeployed position where the free end is located at a first distance from the mid-longitudinal axis of no more than one-half the maximum width of the capsule to a deployed position where the free end is located at a second distance from the mid-longitudinal axis of more than one-half the maximum width of the capsule so that the free end of the distal portion penetrably engages tissue after the device is implanted into the animal.

In another preferred embodiment, the present invention provides a method for a method for subcutaneously implanting a device containing a microchip into a domestic animal, the device having a leading end and a trailing end. The method includes penetrating subcutaneous tissue of the domestic animal with a cannula having a passage and a distal end; moving the device through the passage until the leading end of the device exits the passage at the distal end of the cannula; permitting at least one retention member formed proximate the leading, end of the device to move into engagement with subcutaneous tissue of the domestic animal; withdrawing the cannula so that the trailing end of the device exits the passage at the distal end of the cannula; and permitting at least one retention member formed proximate the trailing end of the device to move into engagement with the tissue of the domestic animal during the withdrawal of the cannula.

As used herein, the term "capsule" is a vessel or body, hollow or solid, which is preferably configured to contain at least an identification tag therein.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

DETAILED DESCRIPTION OF THE DRAWINGS

Reference will now be made in detail to the present preferred embodiments of the invention, examples of which are illustrated in the accompanying drawings.

FIGS. 1 to 4 show a preferred embodiment of an implantable identification device 100 having a capsule 102 and two pair of retention members 104, 106, 108 and 110 which are moveable from an undeployed position to a deployed position to penetrably engage the subcutaneous tissue of an animal such as a domestic pet or livestock. The preferred elements of identification device 100 and their interrelationship are described below.

Figure 1:
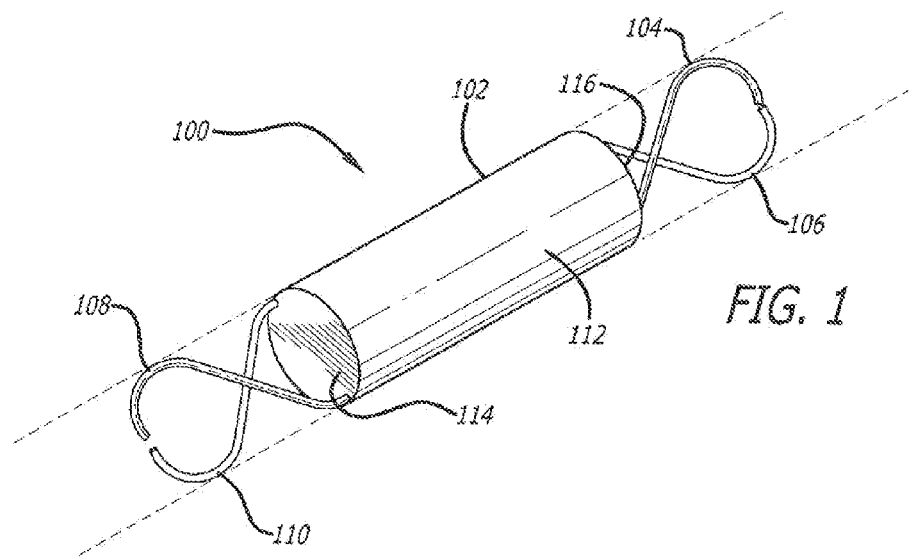
FIG. 1 is a perspective view of an implantable identification device in accordance with a preferred embodiment of the present invention.
Figure 4:
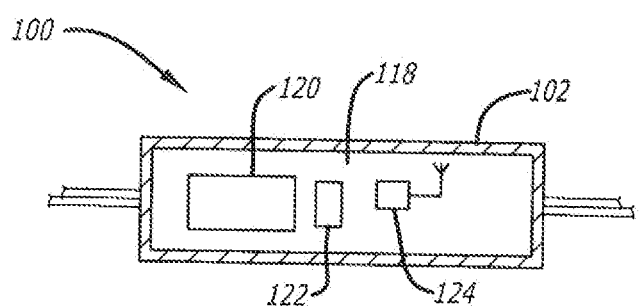
FIG. 4 is a cross-sectional plan view of the identification device of FIG. 1.

Referring to FIG. 1, capsule 102 has a circumferential sidewall 112, a leading surface 114, and a trailing surface 116. Sidewall 112, leading surface 114 and trailing surface 116 preferably define a hollow interior 118, as shown in FIG. 4. Capsule 102 is preferably shaped as a cylinder. The shape of the capsule may be varied without departing from the scope of the present invention.

Sidewall 112 preferably includes a tissue-ingrowth surface to facilitate the integration of identification device 100 with the tissue of the animal into which the identification device is implanted. The tissue-ingrowth surface may have a variety of configurations including, but not limited to, one or more indentations, surface roughenings, recesses, and/or through holes. The surface of the identification device may be impregnated and/or coated with one or more pharmaceutical compositions adapted to reduce trauma to surrounding tissue and/or facilitate tissue ingrowth.

As shown in FIG. 4, hollow interior 118 is preferably is sized and configured to retain a microchip 120, a transmitter 122 and an antenna coil 124. Preferably, hollow interior 118 is devoid of any sensors. Microchip 120 is preferably an identification chip which does not require a self-contained power source to operate. For example only, microchip 120 is preferably a Radio Frequency Identification (RFID) chip, the details of which are understood by those of ordinary skill in the art. Microchip 120 preferably includes pre-determined identification information that is unique to the chip. The pre-determined identification information preferably is a code corresponding to information stored on a database as will be described in more detail below. Preferably, microchip 120 is configured to provide only identification information.

Figure 8:
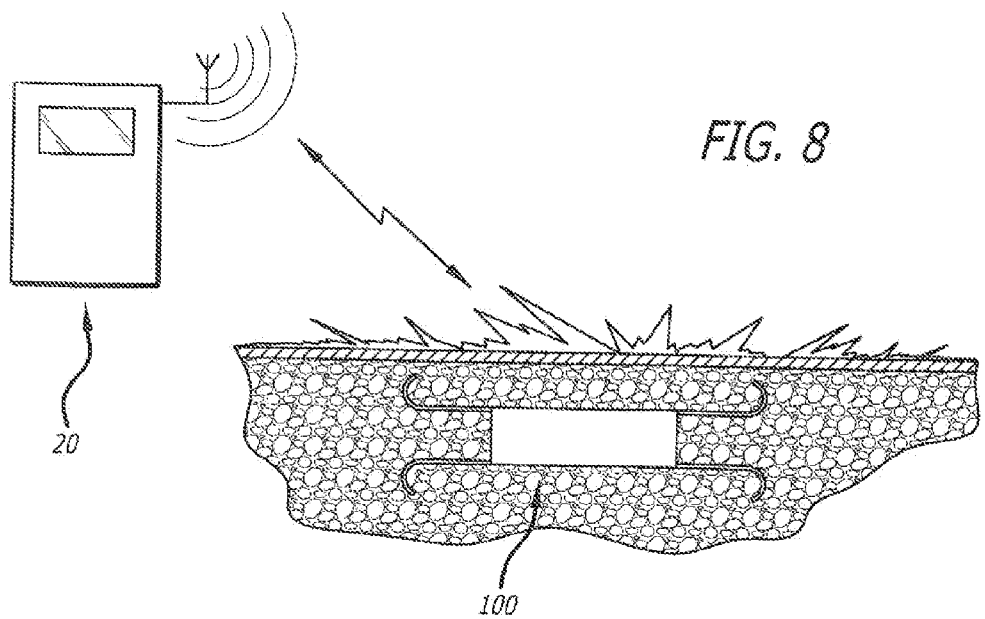
FIG. 8 is a side elevation view of a scanner reading the identification device implanted in the subcutaneous tissue.

Transmitter 122 is preferably configured to transmit information in response to a signal from a scanning device 20 (FIG. 8). Transmitter 122 may be configured to provide location-based information allowing the determination of the animal's current location.

Antenna 124 is operatively connected to transmitter 122. FIG. 4 shows antenna 124 being contained in capsule 102. If desired, the antenna may extend through the exterior of capsule 102. For example only, the antenna may form a portion or the whole of one or more of the retention members. Such a configuration enhances the sensitivity of device 100 to lower signal strength.

Figure 2:
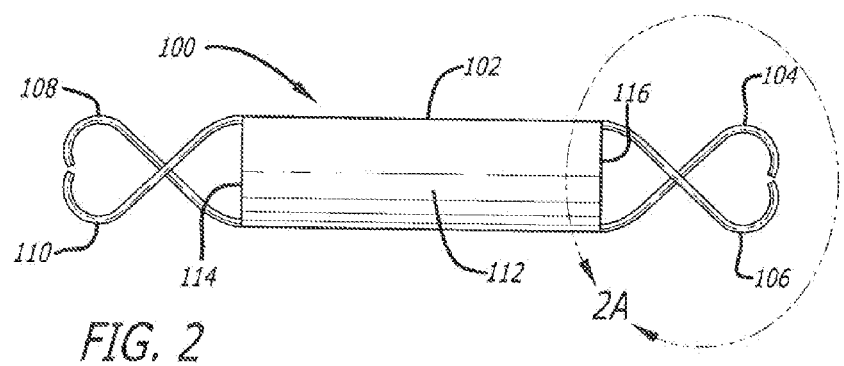
FIG. 2 is a side elevation view of the identification device of FIG. 1.
Figure 2A:
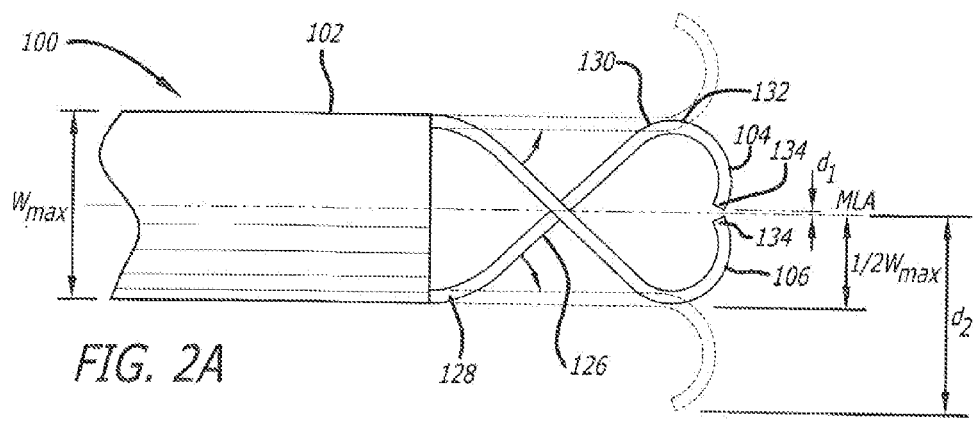
FIG. 2A is a partial expanded view of the trailing end of the identification device of FIG. 1 taken along line 2A of FIG. 2.
Figure 3A:
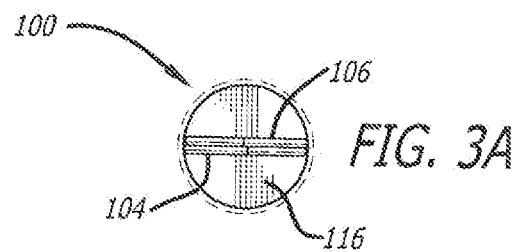
FIG. 3A is a front elevation view of the identification device of FIG. 1.
Figure 3B:
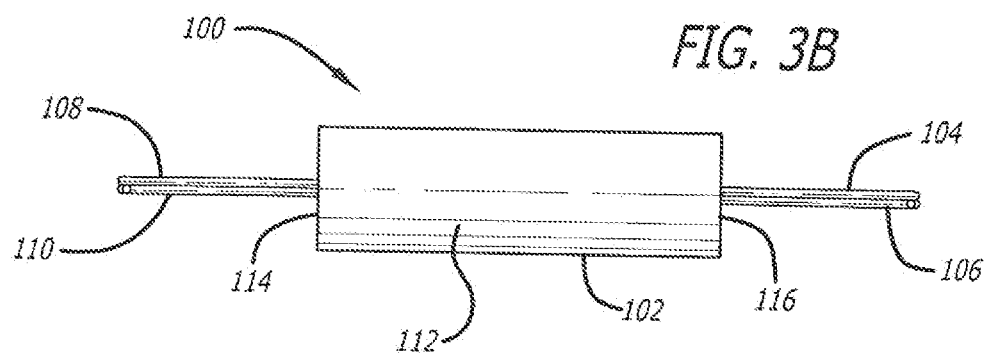
FIG. 3B is a top plan view of the identification device of FIG. 1.

Referring to FIGS. 1, 2 and 2A, identification device 100 preferably includes a pair of retention members 104, 106 extending from trailing surface 116, and a pair of retention members 108, 110 extending from leading surface 114. The retention members preferably extend from the leading and trailing faces rather than side wall 112 so as not to interfere with the deployment of identification device 100 from an insertion tool 10. Retention members 104, 106, 108 and 110 are preferably configured to move from an undeployed position when outside of an animal, to a deployed position when implanted into the animal to penetrably engage the subcutaneous tissue of the animal into which the identification device is implanted. Preferably, the retention members are biased to move from the undeployed position to the deployed position. The preferred movement of the retention members is described further below.

As shown in FIG. 2A, each retention member preferably includes a shaft 126 having a proximal portion 128 where the retention member extends from capsule 102, and an opposite distal portion 130. Distal portion 130 preferably includes at least one bend 132 having an arc of approximately 180 degrees. Distal portion 130 preferably terminates in a free end 134, preferably shaped as a barb. It will be appreciated that the placement and angular measurement of bend 132 may vary without departing from the scope of the present invention. It is also appreciated that in another preferred embodiment, the distal portion need not include a bend or any arc.

The retention members preferably have a maximum length less than the length of capsule 102, the maximum length being measured from the top of bend 132 to the intersection of shaft 126 with capsule 102. This dimension is advantageous in that a more compact identification device reduces the risk of trauma to surrounding tissues. The length of each retention member may be varied as desired, and may be significantly less than the length of capsule 102, for example only, less than half of the length of capsule 102. It is also within the scope of the present invention to have retention members of different lengths at each end, or retention members of a first length at one end and a second, different length at the opposite end of capsule 102.

Retention members 104, 106, 108 and 110 are preferably manufactured from a resilient material such as spring steel or a shape memory material such as Nitinol. Manufacturing the retention members from Nitinol permits identification device 100 to be more compact in the undeployed position, which facilitates the loading of identification device 100 and the deployment of identification device 100 from insertion tool 10.

Figure 5:
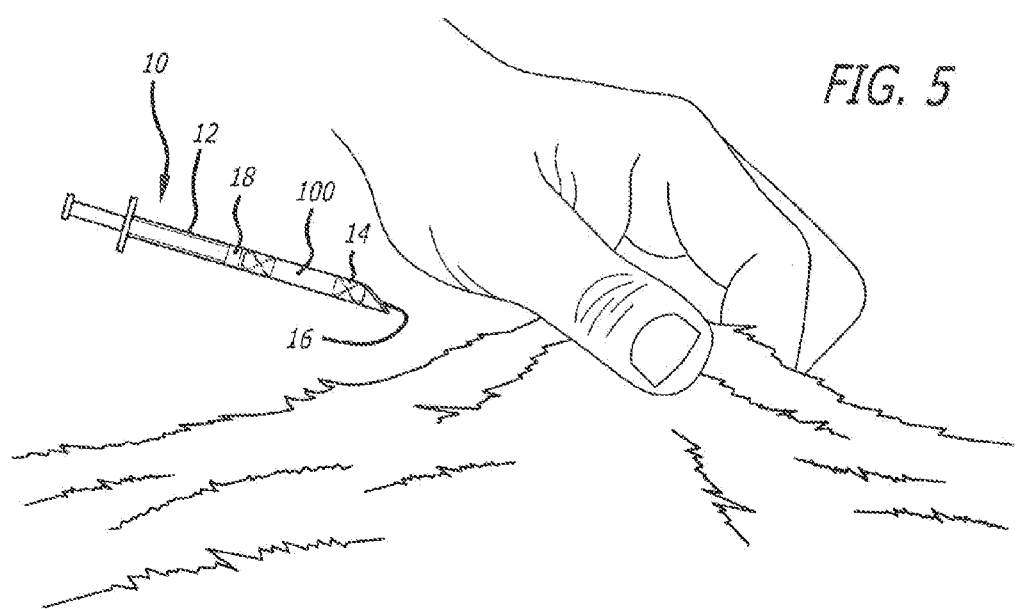
FIG. 5 is a side elevation view of the identification device of FIG. 1 within an insertion tool.

In use, identification device 100 is loaded into insertion tool 10 so that the retention members are pre-loaded into the undeployed position. Referring to FIG. 5, insertion tool 10 preferably includes a trochar needle 12 at one end thereof. Trochar needle 12 has a passage 14 with a distal end 16. Insertion tool 10 also preferably includes a plunger 18 for moving identification device 100 through passage 14.

Referring to FIG. 2A, while in the pre-loaded position, the retention members are preferably confined to the inner diameter of passage 14 of trochar needle 12. The natural bias of the retention members causes each bend 132 to contact the inner surface of passage 14. While in the undeployed position, free end 134 is preferably located at a first distance $d_1$ from the mid-longitudinal axis MLA of no more than one-half the maximum width $W_{max}$ of capsule 102. Once identification device 100 has left the confines of passage 14, each retaining member preferably moves to the deployed position where free end 132 is located at a second distance $d_2$ from the mid-longitudinal axis MLA of more than one-half the maximum width $W_{max}$ of capsule 102 so that free end 132 penetrably engages tissue after identification device 100 is implanted into the animal.

As shown in FIG. 2A, in the undeployed position, shaft 126 of each retention member preferably has an included angle of approximately 45 degrees at proximal portion 128 relating to capsule 102. When deployed, this angle becomes approximately 90 degrees so that a linear portion of shaft 126 is generally parallel to the mid-longitudinal axis of identification device 100 as shown in dotted outline in FIG. 2A.

When in the deployed position, one of the free ends of the pair of the retention members at the trailing end preferably faces one of the free ends of the pair of the retention members at the leading end. Preferably, though not shown, these free ends directly face one another. Preferably, the free end of the retention member at the leading end and the free end of the retention member at the trailing end are co-planar relative to each other and the mid-longitudinal axis while in the deployed position. It will be appreciated that other configurations may be devised, such as that shown in FIGS. 9A and 9B, and described further below.

Having described the preferred components of implantable identification device 100, a preferred method of use will now be described with reference to FIGS. 5 to 8. Referring to FIG. 5, identification device 100 is loaded into passage 14 of insertion tool 10. It will be appreciated that identification device 100 may be provided separately and combined with a re-useable insertion tool, or may be provided as a kit with identification device 100 already loaded in a single-use, disposable insertion tool. While in passage 14, identification device 100 is in its undeployed position with the retention members biased to move away from the mid-longitudinal axis of identification device 100.

Figure 6:
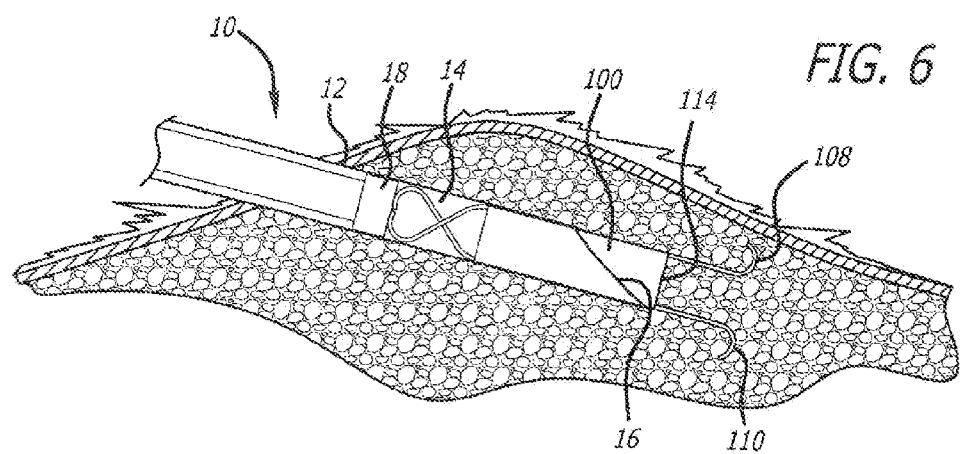
FIG. 6 is a side elevation view of the identification device of FIG. 1 being implanted into subcutaneous tissue.

In FIG. 6, the user engages the tissue of the animal with distal end 16 of trochar needle 12 and moves plunger 18 distally to force identification device 100 into the subcutaneous tissue of the animal. As leading end 114 exits distal end 16 of insertion tool 10, retention members 108, 110 resiliently move to the deployed position away from the mid-longitudinal axis of identification device 100, no longer constrained by the walls of passage 14.

Figure 7:
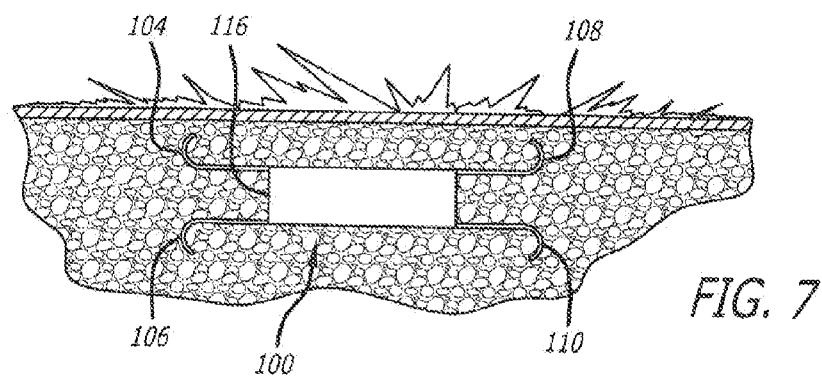
FIG. 7 is a side elevation view of the identification device of FIG. 1 in a deployed position in the subcutaneous tissue.

Referring to FIG. 7, the user continues to move plunger 18 distally to fully disengage identification device 100 from insertion tool 10. As trailing end 116 exits distal end 16 of insertion tool 10, retention members 104, 106 resiliently move to the deployed position away form the mid-longitudinal axis of identification device 100. With all of the retention members in the deployed position, tissue engaged by the retention members is further trapped by a compressive force exerted by opposing retention members from opposite ends, which facilitates identification device 100 being reliably and securely fastened to the tissue.

Preferably, the microchip has a unique identification code associated with biographical information relating to the intended animal into which the microchip is to be implanted. The association may occur prior to implantation and/or after implantation. Such information may include, without limitation, any one or more of the pet's name, breed, birth date, owner information such as owner name, address, phone number and/or e-mail, known medical conditions, and veterinarian contact details. This information may be stored on a database and associated with a unique code stored on the chip which may include at least one of text, symbols, and numbers. The unique code may be randomly generated, or selected by the owner. For example only, the owner or some other individual may program the microchip with a unique code memorable to that individual, such as a pin number, birth date, social security number, or some other personal identification information.

The biographical information may be stored directly onto the chip, but it is preferable to use a code on the chip and store the biographical information in a remote database so that the biographical information may be modified or updated with greater ease. Storing the biographical information in the database provides several advantages. For example, should the owner change addresses or contact details, the biographical information may be updated with less difficulty so that should the pet become lost, the owner may be contacted using their current contact details. As a result, the system does not become obsolete every time an owner moves or changes contact details.

Some time after implantation, a user may read identification information contained in identification device 100 by using a reader or scanning device 20, shown in FIG. 8. Scanning device 20 may be operatively connected to the remote database, or may include a biographical information database therein. It will be appreciated that the steps described above may be performed in a different order, varied, or some steps omitted entirely without departing from the scope of the present invention.

The reading of microchips, such as RFID tags, by scanning devices will be appreciated by those of ordinary skill in the art. Preferably, the scanning device is a hand-held portable device. It will be appreciated that the scanning device may be a stationary device similar to airport scanners or security scanners placed at exits of retail stores. Stationary scanners have many beneficial uses in the pet environment, such as at the entry of pet shows to easily identify a competitor, or at airports to identify a pet that is travelling.

The present system may be used with both a hand-held scanner and a stationary scanner. For example, a hand-held scanner may be used with the identification device to register or check-in the pet at a veterinarian and/or kennel. In such a situation, the biographical information associated with the pet may include billing account information. It will be appreciated that the certain aspects of the present invention are adaptable to a wide variety of applications.

Figure 9A:
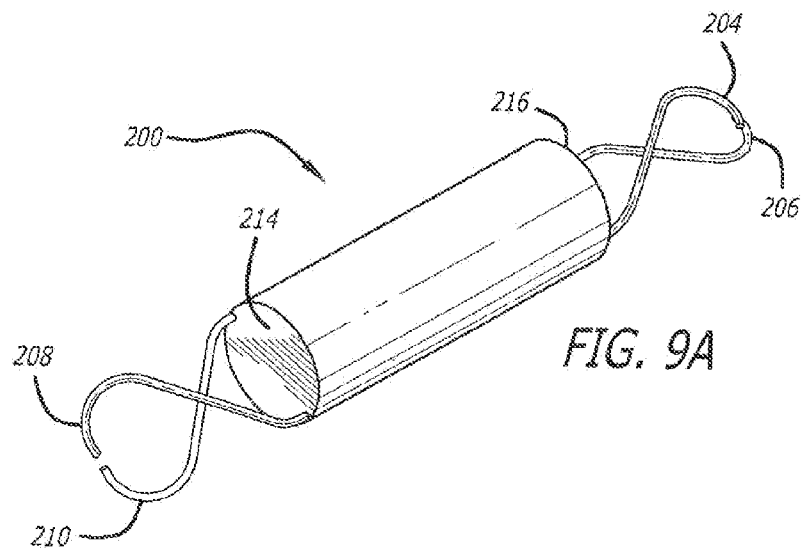
FIG. 9A is a perspective view of an identification device in accordance with another preferred embodiment of the present invention.
Figure 9B:
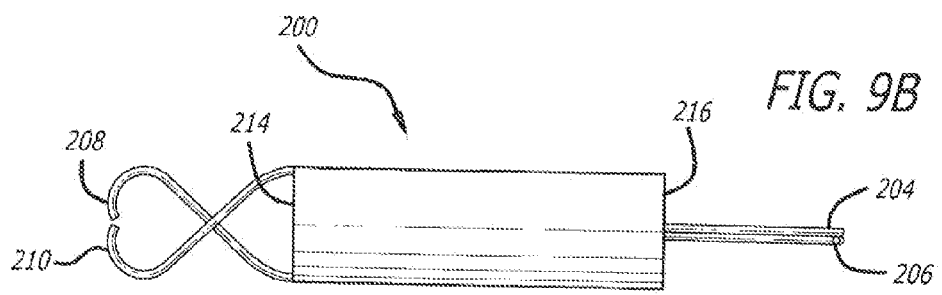
FIG. 9B is a side elevation view of the identification device of FIG. 9A.

Referring now to FIGS. 9A and 9B, an implantable identification device 200 is shown in accordance with another preferred embodiment of the present invention. Device 200 is similar to identification device 100 except that a first plane including retention members 208, 210 at leading end 214 is perpendicular to a second plane including retention members 204, 206 at trailing end 216. The embodiment shown in FIGS. 9A and 9B is just one example of how the number, placement, shape and material of the retention members may be varied without departing from the scope of the invention. Additionally, the identification device may include anywhere from one to more than four retention members. The retention members may extend from only one end of the capsule. The retention members may be directly opposite one another in a plane coplanar with the mid-longitudinal axis of the identification device, or may be non-coplanar with the mid-longitudinal axis. The retention members at one or both ends may be equal-distant from each other. For example, where there are three retention members at one end, they may be positioned approximately 120 degrees apart relative to the mid-longitudinal axis of identification device 100.

The foregoing description is by way of example only, and may be varied considerably without departing from the scope of the present invention. For example only, the retention member may be configured in different shapes. The retention member may be twisted, and/or include a plurality of surface engaging features such as barbs.

The capsule may include a hollow interior, as described above, or may be solid with microchip 120 molded into the solid structure. The capsule may be fitted with global positioning technology (GPS) to facilitate locating a lost pet. The method described above may include locating a lost animal carrying a capsule having GPS technology. The identification device may find applications for use in identifying humans.

The features described with respect to one embodiment may be applied to other embodiments, or combined with or interchanged with the features of other embodiments, as appropriate, without departing from the scope of the present invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A self-anchoring, implantable identification device for use in identifying an animal, comprising:
    a capsule having a leading end with a forward facing surface, a trailing end, a mid-longitudinal axis through said leading and trailing ends, a length from said leading end to said trailing end along the mid-longitudinal axis, and a maximum width perpendicular to the mid-longitudinal axis;
    a microchip sized and configured for placement in said capsule of said device, said microchip being configured to store identification information unique to the microchip for identification of the animal into which said device is implanted, the identification information including at least one of text, symbols, and numbers;
    a transmitter for transmitting the identification information stored on said microchip;
    an antenna operatively connected to said transmitter; and
    at least one retention member extending from said forward facing surface of said leading end of said capsule, said retention member having a proximal portion and a distal portion with a free end, said retention member when extended from said forward facing surface being biased to move from an undeployed position where said free end is located at a first distance from the mid-longitudinal axis of no more than one-half the maximum width of said capsule to a deployed position where said free end is located at a second distance from the mid-longitudinal axis of more than one-half the maximum width of said capsule so that said free end of said distal portion penetrably engages tissue after said device is implanted into the animal.

2. The device of claim 1, wherein said microchip is a RFID microchip.

3. The device of claim 1, wherein said capsule is generally cylindrical.

4. The device of claim 1, wherein said free end of said retention member is formed as a barb.

5. The device of claim 1, wherein said retention member includes a bend that has an arc of approximately 180 degrees.

6. The device of claim 1, wherein said proximal portion of said retention member includes a linear portion, said linear portion being parallel to the mid-longitudinal axis of said capsule when said retention member is in the deployed position.

7. The device of claim 1, wherein said retention member comprises at least in part Nitinol.

8. The device of claim 1, wherein said transmitter is configured to provide location-based information allowing determination of the animal's current location.

9. The device of claim 1, wherein said capsule includes a tissue-ingrowth surface.

10. The device of claim 9, wherein said tissue-ingrowth surface includes a plurality of recesses.

11. The device of claim 9, wherein said tissue-ingrowth surface includes at least one through-hole.

12. The device of claim 1, in combination with an insertion device configured to deploy said device into the animal.

13. The device of claim 1, wherein both of said leading and trailing ends of said capsule include said at least one retention member.

14. The device of claim 13, wherein said free end of said retention member at said leading end and said free end of said retention member at said trailing end directly face each other in the deployed position.

15. The device of claim 13, wherein said free end of said retention member at said leading end is in a first plane co-planar with the mid-longitudinal axis, and said free end of said retention member at said trailing end is in a second plane co-planar with the mid-longitudinal axis, said first and second planes being generally perpendicular to one another in the deployed position.

16. The device of claim 13, wherein said free end of said retention member at said leading end and said free end of said retention member at said trailing end are co-planar relative to each other and the mid-longitudinal axis in the deployed position.

17. The device of claim 1, wherein said forward facing surface lies in a plane perpendicular to the mid-longitudinal axis of said capsule.

18. The device of claim 1, wherein the identification information is a code corresponding to information stored on a database.

19. The device of claim 1, wherein the identification information is a code created by an owner of the animal.

20. The device of claim 1, wherein said antenna forms at least a portion of said retention member.

21. A self-anchoring, implantable identification device for use in identifying an animal, comprising:
    a capsule having a leading end, a trailing end, a mid-longitudinal axis through said leading and trailing ends, a length from said leading end to said trailing end along the mid-longitudinal axis, and a maximum width perpendicular to the mid-longitudinal axis;
    a microchip sized and configured for placement in said capsule of said device, said microchip being configured to store identification information unique to the microchip for identification of the animal into which said device is implanted, the identification information including at least one of text, symbols, and numbers;
    a transmitter for transmitting the identification information stored on said microchip;
    an antenna operatively connected to said transmitter; and
    at least one retention member extending from a forward facing surface of said leading end of said capsule of said device, said retention member having a proximal portion and a distal portion with a free end, said retention member having a maximum length that is less than the length of said capsule, said retention member when extended from said forward facing surface being biased to move from an undeployed position where said free end is located at a first distance from the mid-longitudinal axis of no more than one-half the maximum width of said capsule to a deployed position where said free end is located at a second distance from the mid-longitudinal axis of more than one-half the maximum width of said capsule so that said free end of said distal portion penetrably engages tissue after said device is implanted into the animal.

22. The device of claim 21, wherein said microchip is a RFID microchip.

23. The device of claim 21, wherein said capsule is generally cylindrical.

24. The device of claim 21, wherein both of said leading and trailing ends of said capsule include said at least one retention member.

25. The device of claim 21, wherein said free end of said retention member is formed as a barb.

26. The device of claim 21, wherein said retention member includes a bend that has an arc of approximately 180 degrees.

27. The device of claim 21, wherein said proximal portion of said retention member includes a linear portion, said linear portion being parallel to the mid-longitudinal axis of said capsule when said retention member is in the deployed position.

28. The device of claim 21, wherein said retention member comprises at least in part Nitinol.

29. The device of claim 21, wherein said transmitter is configured to provide location-based information allowing determination of the animal's current location.

30. The device of claim 21, wherein said capsule includes a tissue-ingrowth surface.

31. The device of claim 30, wherein said tissue-ingrowth surface includes a plurality of recesses.

32. The device of claim 30, wherein said tissue-ingrowth surface includes at least one through-hole.

33. The device of claim 21, in combination with an insertion device configured to deploy said device into the animal.

34. The device of claim 21, wherein the identification information is a code corresponding to information stored on a database.

35. The device of claim 21, wherein the identification information is a code created by an owner of the animal.

36. The device of claim 21, wherein said antenna forms at least a portion of said retention member.

37. A method for subcutaneously implanting a device containing a microchip into a domestic animal, the device having a leading end, a trailing end, a mid-longitudinal axis through the leading and trailing ends, and a maximum width perpendicular to the mid-longitudinal axis, the method comprising:
  penetrating subcutaneous tissue of the domestic animal with a cannula having a passage and a distal end;
  moving the device through the passage until the leading end of the device exits the passage at the distal end of the cannula;
  permitting at least one retention member extending from a forward facing surface of the leading end of the device to move into engagement with subcutaneous tissue of the domestic animal, the retention member having a proximal portion and a distal portion with a free end, the retention member when extended from the forward facing surface being biased to move from an undeployed position where the free end is located at a first distance from the mid-longitudinal axis of no more than one-half the maximum width of the device to a deployed position where the free end is located at a second distance from the mid-longitudinal axis of more than one-half the maximum width of the device so that the free end of the distal portion penetrably engages the tissue of the domestic animal;
  withdrawing the cannula so that the trailing end of the device exits the passage at the distal end of the cannula; and
  permitting at least a second retention member extending from a rearward facing surface of the trailing end of the device to move into engagement with the tissue of the domestic animal during the withdrawal of the cannula.

38. The method of claim 37, further comprising recording in a database identification information particular to the domestic animal into which the device is implanted.

39. The method of claim 38, further comprising modifying the identification information recorded in the database based on a change of address of an owner of the domestic animal.

40. The method of claim 38, wherein the identification information includes ownership information of the domestic animal.

41. The method of claim 37, wherein the microchip is a RFID chip.

42. The method of claim 37, wherein the device has a length, the at least one retention member having a maximum length that is less than the length of the device.

* * * * *

UNITED STATES PATENT AND TRADEMARK OFFICE
CERTIFICATE OF CORRECTION

| | | |
|---|---|---|
| PATENT NO. | : 8,922,373 B2 | Page 1 of 1 |
| APPLICATION NO. | : 13/440825 | |
| DATED | : December 30, 2014 | |
| INVENTOR(S) | : Gary Karlin Michelson | |

It is certified that error appears in the above-identified patent and that said Letters Patent is hereby corrected as shown below:

Title Page 1, Item (73), Assignee:

Change "Foundation Animals Foundation, Inc." to --Found Animals Foundation, Inc.--.

Signed and Sealed this
Fourteenth Day of April, 2015

Michelle K. Lee
*Director of the United States Patent and Trademark Office*